United States Patent
Haase et al.

(10) Patent No.: US 11,419,571 B2
(45) Date of Patent: Aug. 23, 2022

(54) X-RAY SYSTEM ERROR TRACKING AND CALIBRATION

(71) Applicant: KONINKLIJKE PHILIPS N.V., Eindhoven (NL)

(72) Inventors: Christian Haase, Hamburg (DE); Michael Grass, Buchholz in der Nordheide (DE); Dirk Schafer, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 77 days.

(21) Appl. No.: 17/047,103

(22) PCT Filed: Apr. 5, 2019

(86) PCT No.: PCT/EP2019/058720
§ 371 (c)(1),
(2) Date: Oct. 13, 2020

(87) PCT Pub. No.: WO2019/197299
PCT Pub. Date: Oct. 17, 2019

(65) Prior Publication Data
US 2021/0153836 A1   May 27, 2021

(30) Foreign Application Priority Data
Apr. 13, 2018  (EP) .................................... 18167262

(51) Int. Cl.
*G01D 18/00*      (2006.01)
*A61B 6/00*       (2006.01)

(52) U.S. Cl.
CPC ............ *A61B 6/584* (2013.01); *A61B 6/4441* (2013.01); *A61B 6/5205* (2013.01); *A61B 6/586* (2013.01)

(58) Field of Classification Search
CPC ...... A61B 6/586; A61B 6/4441; A61B 6/5205; A61B 6/584; A61B 6/4085; A61B 6/4464;
(Continued)

(56) References Cited

U.S. PATENT DOCUMENTS 10,874,371 B2 * 12/2020 Gorges .................. A61B 6/581
2008/0089566 A1 *  4/2008 Node-Langlois ......... G06T 7/30
                                                                382/128
(Continued)

FOREIGN PATENT DOCUMENTS

DE        102013206113 A1     10/2014

OTHER PUBLICATIONS

PCT/EP2019/058720 ISR & WO, May 29, 2019, 12 Page Document.
(Continued)

*Primary Examiner* — Irakli Kiknadze

(57) ABSTRACT

Mechanical image acquisition systems (such as medical C-arms) frequently accumulate geometrical errors which must be calibrated out using a calibration phantom. A more frequent regime of system calibration implies a less frequent use of the C-arm for clinical applications. The present application proposes to identify common biases between the acquired projection frame sequences from the same mechanical image acquisition system in first and second acquisitions, and to compare this to expected calibration data of the mechanical image acquisition system to generate frame deviation measures. If a resemblance between the first and second sequences of frame deviation measures is obtained, one or more calibration actions are performed (such as alerting the user that calibration should be provided, and/or automatically correcting for the geometry deviation).

14 Claims, 5 Drawing Sheets

(58) Field of Classification Search
CPC ..... A61B 6/0492; A61B 90/39; A61B 6/4405;
A61B 6/542; A61B 6/032; A61B 6/583;
A61B 6/581; A61B 6/582; A61B 6/5258;
A61B 6/547; A61B 6/587; A61B 6/486;
A61B 6/507; A61B 6/4014; A61B 6/027;
A61B 6/5264; A61B 6/035; G16H 40/63;
G16H 30/40; G01N 23/04; G01N
2223/303; G01N 23/046; G06T 11/003;
G06T 11/005; G06T 2210/41; G06T
2211/412; G06T 5/006; G06T 7/0012;
G06N 3/08; G06N 3/0454
USPC ........................................................ 378/207
See application file for complete search history.

(56) References Cited

U.S. PATENT DOCUMENTS

| | | |
|---|---|---|
| 2010/0191371 A1 | 7/2010 | Hornung et al. |
| 2014/0228678 A1* | 8/2014 | Meyer .................. A61B 6/5235 600/424 |
| 2015/0199813 A1 | 7/2015 | Yamahana et al. |
| 2017/0231596 A1 | 8/2017 | Fieselmann et al. |

OTHER PUBLICATIONS

Ouadah et al.: "Self-Calibration of Cone-Beam CT Geometry Using 3D-2D Image Registration" Phys Med Biol. Apr. 7, 2016, 61(7), pp. 2613-2632.

* cited by examiner

X-RAY SYSTEM ERROR TRACKING AND CALIBRATION

CROSS-REFERENCE TO PRIOR APPLICATIONS

This application is the U.S. National Phase application under 35 U.S.C. § 371 of International Application No. PCT/EP2019/058720, filed on Apr. 5, 2019, which claims the benefit of European Patent Application No. 18167262.7, filed on Apr. 13, 2018. These applications are hereby incorporated by reference herein.

FIELD OF THE INVENTION

This invention relates generally to an apparatus for X-Ray system error tracking and calibration, and an associated method, X-Ray imaging system, a computer program element, and a computer readable medium.

BACKGROUND OF THE INVENTION

Modern X-Ray acquisition systems enable high-quality volumetric reconstructions of a region of interest to be obtained directly at the site of use. A typical use of an X-Ray acquisition system is as part of a C-arm imaging system. As the C-arm is moved to different positions, mechanical deflections cause it to change geometry.

Accordingly, the C-arm has to be calibrated in a dedicated calibration acquisition, using a dedicated calibration phantom having predictable geometry. Comparing an acquired image of the calibration phantom obtained using various orbits of the C-arm imaging system with the expected image of the calibration phantom at the same orbits enables calibration coefficients of the C-arm imaging system to be calculated and applied.

However, the need to provide a calibration phantom, and to regularly perform calibration steps, using it is onerous. US 2017/0231596 A1 discusses an X-Ray system calibration system which evaluates images of a calibration phantom to ascertain calibration parameters of an X-Ray system. Such systems can, however, be further improved.

SUMMARY OF THE INVENTION

Accordingly, it would be advantageous to provide an improved technique for X-Ray system error tracking and calibration.

According to a first aspect, there is provided an apparatus for performing error tracking and calibration of a mechanical image acquisition system. The apparatus comprises:
an input unit; and
a processing unit.

The input unit is configured to acquire at least first and second 2D projection frame sequences of an examination area of the mechanical image acquisition system at different times using the same mechanical image acquisition system in first and second acquisitions, and to acquire expected calibration data defining an expected calibrated geometry of the mechanical image acquisition system.

According to a first aspect, there is provided an apparatus for performing error tracking and calibration of a mechanical image acquisition system. The apparatus comprises:
an input unit; and
a processing unit.

The input unit is configured to acquire at least first and second 2D projection frame sequences of an examination area at different times using the same mechanical image acquisition system in first and second acquisitions, and to acquire expected calibration data defining an expected calibrated geometry of the mechanical image acquisition system.

The processing unit is configured to apply rigid motion compensation separately to at least the first and second 2D projection sequences and to compare the compensated first and second 2D projection sequences separately to the expected calibrated geometry, to thus generate a first sequence and a second sequence of frame deviation measures representing a geometric deviation of the mechanical image acquisition system from the expected calibrated geometry occurring during the first and second acquisitions, to determine a resemblance between the first sequence of frame deviation measures and the second sequence of frame deviation measures, and, if a resemblance between at least one corresponding portion of the first and second sequences of the frame deviation measures is determined, to perform one or more calibration actions.

Accordingly, it is possible to identify a deviation of the calibration of the X-Ray imaging system from the expected calibration of the X-Ray imaging system using two projection sequences acquired in normal use of the X-Ray imaging system and the expected calibrated geometry. Thus, a need to perform a dedicated calibration procedure using the X-Ray imaging system in combination with an X-Ray calibration phantom is reduced. For example, this may have to be done only when a deviation in the projection sequences with respect to the expected calibration has been identified, rather than at regular intervals. Accordingly, the X-Ray imaging system has a higher availability.

Optionally, the processing unit is further configured to apply rigid motion compensation separately to at least the first and second 2D projection sequences by: generating respective first and second initial 3D reconstructions of the first and second 2D projection sequences, registering the first initial 3D reconstruction to the first 2D projection frame sequence thereby to generate a first frame offset vector; and registering the second 3D initial 3D reconstruction to the second 2D projection frame sequence thereby to generate a second frame offset vector.

Registration enables a common deviation of the orientation of first and second initial 3D reconstructions from their expected orientations to be identified, thus implying a calibration error of the X-Ray imaging system.

Optionally, the processing unit is further configured to apply rigid motion compensation separately to at least the first and second 2D projection sequences by generating the first and second sequences of frame deviation measures iteratively by optimizing a first and a second image quality statistic in successive reconstructions of the respective first and second 2D projection sequences.

By generating more than one 3D reconstruction of the first and second 2D projection sequences, it is possible to iteratively optimize the rigid motion compensation of the first and second 2D projection sequences using an image quality statistic such as feature sharpness, the pervasiveness of "ring artefacts", and many other image quality statistics. Accordingly, a more accurate assessment of system calibration state can be obtained.

Optionally, the input unit is further configured to receive deviation threshold data of the acquisition system. The processing unit is further configured to identify a first measured deviation of the mechanical image acquisition system from the expected calibration geometry based on a difference between the expected calibration geometry and at least one matching or corresponding portion of the first and second sequences of frame deviation measures for which a resemblance has been determined, and if the first measured deviation exceeds a threshold in the deviation threshold data, to perform the calibration action by displaying to a user a maintenance prompt, and/or to transmit a maintenance request over a data communication network to an external maintenance server.

Accordingly, a maintenance request is displayed, or maintenance may be automatically scheduled if the deviations exceed a predefined threshold.

A given deviation of the X-Ray imaging system geometry from its calibrated geometry might only be harmful to image quality once the deviation has exceeded a certain level. This embodiment tracks the deviation of the X-Ray imaging system geometry against a threshold amount representing a tolerable level of deviation of the X-Ray system from the calibrated geometry.

Optionally, the input unit is further configured to acquire a third 2D projection frame sequence, at a subsequent time to the first and second 2D projection frame sequences.

The processing unit is further configured to determine a corresponding third sequence of frame deviation measures of the third 2D projection frame sequence from the expected calibrated geometry, to identify resemblance between the first and/or second sequence and the third sequence of the frame deviation measures, to identify a second measured deviation of the mechanical image acquisition system from the expected calibration geometry between the first and/or second and the third sequences of the frame deviation measures based upon the resemblance between the portions of the second and third sequences of the frame deviation measures, and to predict, using a rate of change of the difference between the first and second measured deviations, a scheduling time of a future maintenance period. The calibration action comprises transmitting the scheduling time of the future maintenance period over a data communication network to an external maintenance server, and/or displaying the scheduling time to a user.

Accordingly, the maintenance period of the X-Ray imaging system may be more accurately scheduled, leading to an optimal amount of use-time of the X-Ray imaging system at a tolerable system accuracy.

In an example, further 2D projection frame sequences may be acquired and processed in a similar manner so as to further increase the scheduling accuracy.

The identification of a plurality of deviations of the X-Ray imaging system across a wider timeframe enables the tracking of calibration errors, and an assessment be made as to whether or not the calibration error is increasing linearly, or geometrically, for example. With at least two measured deviations, and knowledge of the time in between them, a prediction may be calculated defining when the calibration error will become unacceptable and require calibration.

Optionally, the processing unit is further configured to estimate a first corrected trajectory of the mechanical image acquisition system during the acquisition of the first 2D projection sequence based on the first sequence of frame deviation measures, and estimating a second corrected trajectory of the mechanical image acquisition system during the acquisition of the second mechanical image acquisition system projection sequence based on the second sequence of frame deviation measures.

The identification of a corrected trajectory enables the processing unit to "feed-back" updates to the drive system of an X-Ray imaging system to account for mechanical calibration errors. Although ultimately mechanical recalibration of the X-Ray imaging system will still be needed, it is possible to lengthen the amount of useful operative time of the X-Ray imaging system (in other words, to extend the amount of time between maintenance) by biasing the electronic commands for commanding the X-Ray imaging system into a certain position at a certain time using the corrected trajectory.

Optionally, the processing unit is further configured to identify selected portions of the first and second corrected trajectories having a significant similarity to each other; and to calculate calibration difference data between the selected portions and the expected calibrated trajectory. The processing unit is further configured to perform the calibration action by acquiring a third 2D projection frame sequence and applying the calibration difference data to generated a corrected third 2D projection frame sequence.

Optionally, the input unit is further configured to acquire a trajectory characteristic database comprising example trajectory data of historical geometry deviations of the mechanical image acquisition system. The processing unit is further configured to perform as the calibration action: comparing at least one of the selected portions of the first and second corrected trajectories to the example trajectory data in the trajectory characteristic database, and confirming that the at least one of the selected portions of the first and second corrected trajectories resembles a historical geometry deviation of the mechanical image acquisition system.

The same X-Ray imaging system may suffer from a repeated calibration error caused by an installation error, or a particular usage characteristic of a medical institution, for example institution might focus on dental examination, using only a small subset of orbits of the X-Ray imaging system and causing more wear of the components involved in providing small subset of orbits. Accordingly, by recording historical geometry deviations of the mechanical image acquisition system, it is possible to diagnose, for example, the cause of certain present geometry deviations an X-Ray imaging system.

Optionally, the input unit is further configured to receive and/or automatically identify an acquisition protocol of the mechanical image acquisition sequence used during the acquisition of the first and/or second 2D projection frame acquisition sequences. The processing unit is further configured to perform as the calibration action assigning a confidence level to the first sequence of frame deviation measures based upon the acquisition protocol.

An X-Ray imaging system is provided with a sequence of electronic commands before the acquisition of a patient according to a particular orbit. By identifying geometry deviations at certain points of the system's orbit, it is possible to provide an accuracy assessment at certain times of an acquired sequence.

Optionally, the input unit is further configured to receive and/or automatically identify what object or what part of a patient is imaged by the mechanical image acquisition system during the acquisition of the first and/or second 2D projection frame acquisition sequences. The processing unit is further configured to perform as the calibration action assigning a confidence level to the first sequence of frame deviation measures based upon the object or the part of the human body that is imaged.

Optionally, the first sequence and a second sequence of frame deviation measures comprise a first and second sequence of magnitudes representing the magnitude of respective first and second offset vectors from an ideally calibrated case.

Optionally, the mechanical image acquisition system is a C-arm.

According to a second aspect there is provided an error tracking method for calibrating a mechanical image acquisition system, comprising:
a) acquiring at least first and second 2D projection frame sequences of an examination area of the mechanical image acquisition system at different times using the same mechanical image acquisition system in first and second acquisitions;
b) acquiring expected calibration data defining an expected calibrated geometry of the mechanical image acquisition system;
c) applying rigid motion compensation separately to at least the first and second 2D projection sequences and comparing the compensated first and second 2D projection sequences separately to the expected calibrated geometry, to thus generate a first sequence and a second sequence of frame deviation measures representing a geometric deviation of the mechanical image acquisition system from the expected calibrated geometry occurring during the first and second acquisitions;
d) determining a resemblance between the first sequence of frame deviation measures and the second sequence of frame deviation measures; and if a resemblance between at least one portion of the first and second sequences of the frame deviation measures is determined, performing one or more calibration actions.

According to a third aspect there is provided an X-Ray imaging system comprising:
an X-Ray source;
an X-Ray detector; and
an apparatus for performing error tracking and calibration of a mechanical image acquisition system according to the first aspect or its embodiments.

The X-Ray source is configured to sequentially illuminate a region of interest with X-Ray radiation from a first plurality of acquisition angles.

The X-Ray detector is configured to receive the X-ray radiation having propagated via the region of interest from a second plurality of acquisition angles to form an input projection image sequence comprising at least first and second 2D X-Ray projection data acquired, respectively, at first and second acquisition times of a region of interest of a patient.

The apparatus for performing error tracking and calibration of a mechanical image acquisition system is configured to receive the first and second 2D X-Ray projection data from the X-Ray detector, and the apparatus is configured to receive expected calibration data defining an expected calibrated geometry of the X-Ray imaging system from the X-Ray imaging system.

According to a fourth aspect there is provided a computer program element for controlling a processing unit and/or system according to the first and/or third aspects, which, when the computer program element is executed by the processor and/or system, is adapted to perform the method of the second aspect.

According to a fifth aspect there is provided a computer readable medium having stored the computer program element of the fourth aspect.

In the following application, the "2D projection frame sequences" are obtained, for example, using an acquisition approach such as "cone beam CT" in which a divergent two-dimensional X-Ray beam is directed through a region of interest of a patient towards a two-dimensional X-Ray detector.

In the following application, the "2D projection frame sequences" comprise a plurality of "2D X-Ray projection data" representing received pixel values (tracking X-ray intensity and/or energy) from the X-ray detector, as affected by the acquisition system geometry, the source, detector and/or iso-center position and orientation, the patient and or table position and orientation, the time of image acquisition, or any related parameters of the image acquisition.

In the following application, the term "mechanical image acquisition system" typically refers to a "C-arm" X-Ray imaging system although may also relate to any other form of mechanical image acquisition means in which mechanical deviation over time can lead to inaccuracy, such as a CT scanner, a tomographic X-Ray scanner for mammography, an MRI scanner, a fluoroscopy scanner, and the like.

In the following application, the term "an examination area of the mechanical image acquisition system" means a space that an object may be positioned in, so that the mechanical image acquisition system can obtain an image and/or a frame sequence of the object. For example, the "examination area" may refer to the 3D space containing an object that a C-arm's orbit may encircle during an acquisition. It will be appreciated that at different times, different objects (a first or a second patient) may be present in the examination area, or alternatively that the same object (patient) may be imaged at two separate time points.

In the following application, the term "different times" means that the acquisition of the first and second frame sequences is of a different first and a second medical examination using the mechanical image acquisition system. For example, the first frame sequence is of a first patient, and the second frame sequence is of a second patient.

In the following application, the term "geometry of the mechanical imaging system" refers to spatial relationships between, for example, the X-Ray detector and X-Ray source, and their support elements. In a case of a mechanical C-arm, an X-Ray source and an X-Ray detector is arranged on a C-shaped support bracket. In this case, the geometry of the mechanical imaging system is defined at least by the linear separation between the X-Ray source and X-Ray detector, and the angulation in two dimensions of the plane of the X-Ray source with respect to the plane of the X-Ray detector. Therefore, an "expected calibration geometry" in the case of a C-arm refers to an expected value of at least the linear separation between the X-Ray source and X-Ray detector, and the relation of the plane of the X-Ray source with respect to the plane of the X-Ray detector as a consequence of the constructional dimensions of the C-arm, for example. Although a C-arm has been provided as an example, it will be appreciated that the concept of an expected calibration geometry can be extended to many more complicated systems. Accordingly, "expected calibration data" is a computer data structure containing data about the relationship of, for example, the spatial relationship between an X-Ray source and an X-Ray detector in a particular C-arm. If, during a calibration routine, a slight displacement between the X-Ray source and X-Ray detector is identified, this may be recorded in the expected calibration data to thus enable a correction of future measurements, or this identified displacement is used during the further data processing e.g. a tomographic reconstruction.

In the following application, the term "geometric deviation of the mechanical image acquisition system" refers to the mechanical image acquisition system entering an unexpected geometric configuration compared to the expected calibration geometry in use, or over time. As an example referring to C-arm imaging system, it is observed that the C-bracket supporting the X-Ray source and detector pair is ideally assumed to be rigid, but in fact will experience a degree of non-ideal flexure as the C-arm is moved around an orbit. For example, if the C-arm holds the X-Ray source above the X-Ray detector in a perpendicular relationship to the floor supporting the C-arm, and then rotates the C-arm at its bearing 45° clockwise such that the X-Ray source moves around and down towards the floor, and the X-Ray detector moves around and up away from the floor, C-arm bracket will flex to a small but detectable degree as the weight of the X-Ray source attempts to twist the bracket in the direction of gravity. This flexure in the mechanical imaging acquisition system may not be accounted for in the expected calibration data, and thus 2D projection frames acquired as the C-arm travels around its orbit are acquired in a non-ideal geometry.

The skilled person will understand that more complicated mechanical image acquisition systems may comprise many axes (for example 6 axes, or 9 axes), and may circumscribe complicated orbits. The sum of the flexures of the individual mechanical elements providing the many axes results in further geometric deviations which can also be compensated according to the following application.

In the following application, the term "rigid motion compensation" is an image processing technique for aligning an initial 3D reconstruction, or otherwise acquired reference data to a set of 2D projections assuming that a structure in the set of 2D projections, is a rigid object such as bone. This provides based on the 2D image data and the reference data (e.g. the initial 3D reconstruction) a spatially or temporally corrected relation between the imaged object and the image system components.

In the following application, the term "calibration action" means that a message is transmitted to an external computer system, or to a user of the mechanical image acquisition system on a display warning a user that the system must be recalibrated. Optionally, the term "calibration action" may also mean an automatic correction of the expected calibration data once a calibration deviation is identified. In other words, the term "calibration action" can broadly cover the fact that, once a calibration deviation has been identified, a wide range of appropriate courses of action can result, either alone or in combination.

In the following application, the term "resemblance" as applied to two variables means a relationship between the variables which has been caused by a recurring mechanical deficiency (geometrical deficiency, or calibration error calibration error) of a mechanical image acquisition system from which the variables have been obtained. In this application, two rigid motion compensations of at least two imaging sequences taken at different times (optionally with different patients) results in first and second sequences of frame deviation measures. A common mechanical problem between the at least two imaging sequences (such as a slipped calibration encoder in the azimuth joint of the imaging system) will be represented in portions of the first and second sequences of frame deviation measures. The fact that the representations are similar can then be identified, leading to the determination of a resemblance. Many signal processing approaches may be applied to the at least two variables to identify such a resemblance. For example, if the variables represent a spatial deviation caused by a "sag" of an arm of the mechanical image acquisition system, one approach to identifying the resemblance would be to apply a window over portions of the least two variables, and identify a portion where the gradients of the least two variables were within 0.1%, 1%, 2%, 5%, 10%, or 20%, for example. Many other signal comparison approaches could be applied—for example, by applying cross-correlation to the two variables (frame deviation measures), and determining that a resemblance was present above a certain threshold of the cross-correlation between the variables.

Accordingly, it is a basic idea of the application that at least two 2D projection frame sequences may be acquired from multiple patients to detect changes in the geometrical accuracy of a mechanical imaging acquisition system over time. The calibration of the mechanical image acquisition system may be adjusted, or repeated based on geometric deviations from an expected system calibration. The deviations from the expected system calibration are identified by identifying similarities in the at least two 2D projection frame sequences that imply a deviation from the expected system calibration.

In other words, it is proposed to identify common biases between the acquired projection frame sequences from the same mechanical image acquisition system in first and second acquisitions, and to compare this to expected calibration data of the mechanical image acquisition system to generate frame deviation measures. If a resemblance between the first and second sequences of frame deviation measures is determined, one or more calibration actions are performed (such as alerting the user that calibration should be provided, and/or automatically correcting for the geometry deviation).

BRIEF DESCRIPTION OF THE DRAWINGS

Exemplary embodiments will be described with reference to the following drawings.

DETAILED DESCRIPTION OF EMBODIMENTS

Figure 1:
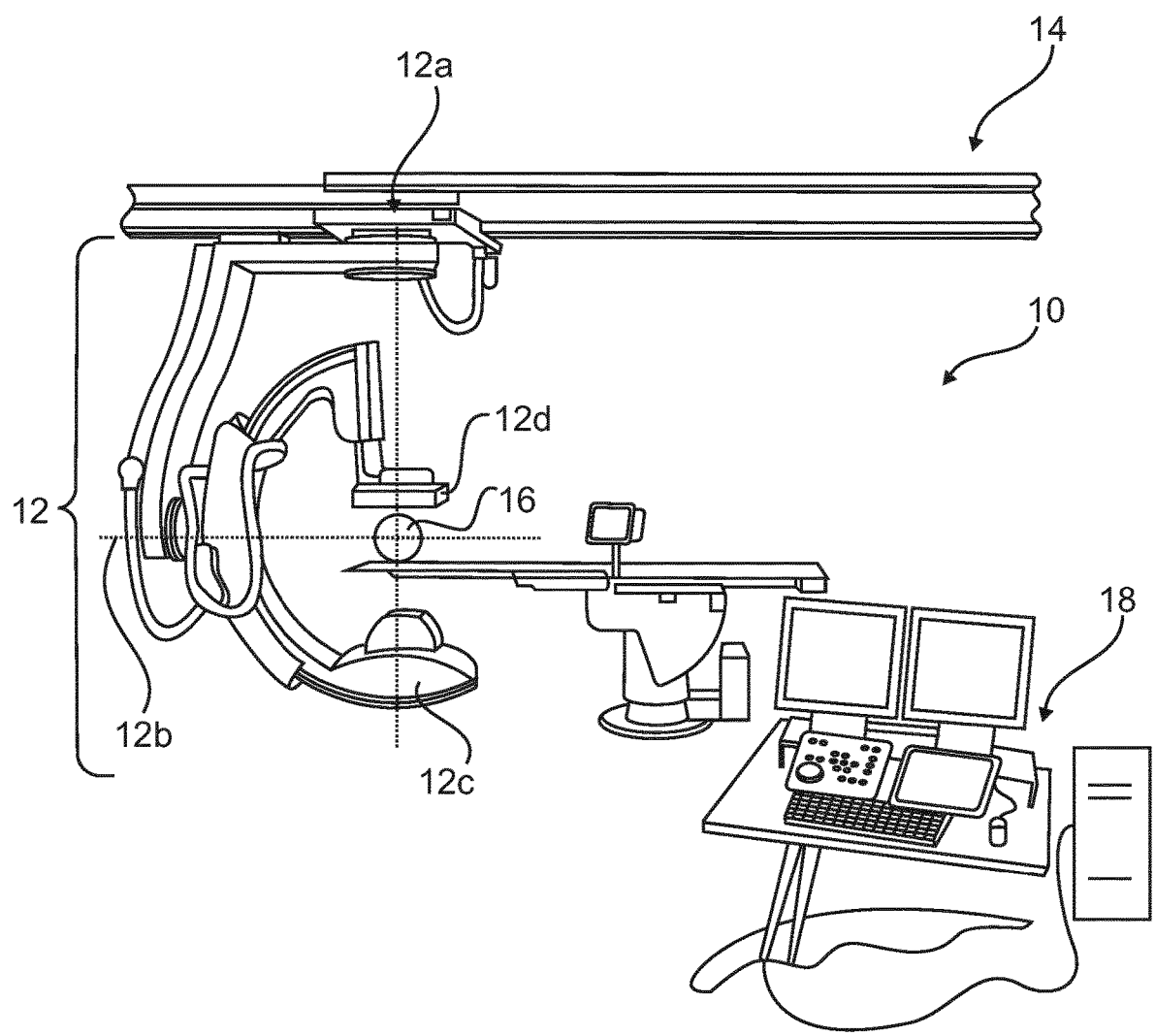
FIG. 1 schematically illustrates an X-Ray imaging system comprising a mechanical image acquisition system.

FIG. 1 illustrates a C-arm acquisition suite 10 (X-Ray imaging system). It is noted that although the C-arm acquisition system, applying the "cone beam computed tomography" technique (CBCT), is a common 3D image acquisition technique, the image acquisition technique is not limited to this acquisition technique.

The C-arm acquisition suite 10 comprises a C-arm 12 attached to the ceiling 14 of the C-arm acquisition suite. The C-arm 12 is attached to the ceiling 14 by a rotatable azimuthal connection 12a, with a rotatable bearing 12b providing a degree of freedom in the inclination direction. An X-Ray source 12c is positioned on a first end of the C-arm 12, facing an X-Ray detector 12d (optionally a digital flat panel detector). An examination area 16 is provided in between the X-Ray source 12c and the X-Ray flat panel detector 12d. Dependent upon the angulation of the X-Ray source 12c and the X-Ray detector 12d with respect to an object (such as a patient's head) in the examination area 16, a sequence of 2D X-Ray projection images may be obtained as the C-arm 12 is moved in an orbit around the examination area 16. The sequence of 2D X-Ray projection images is provided to an apparatus 18 configured to apply a tomographic reconstruction algorithm to the 2D X-Ray projection image sequence, and thus to provide and optionally display a 3D image of the region of interest of a patient in the examination area 16. Typically, the apparatus 18 applies a filtered back projection algorithm, or an iterative reconstruction algorithm to obtain the 3D image of the region of interest of the patient, although many other such tomographic reconstruction algorithms may also be applied.

Although a C-arm mechanical image acquisition system has been illustrated in FIG. 1, the following description applies to any image acquisition system with a movable mechanical element supporting the imaging detectors (for example an X-Ray source and X-Ray detector pair).

For example, in the C-arm 12 illustrated in FIG. 1, the azimuthal connection 12a and the rotatable bearing 12b introduce degrees of rotational inaccuracy. The C-bracket supporting the X-Ray source 12d and the X-Ray detector 12d is attached to the rotatable bearing 12b by a linear motor that functions to enable the C-bracket to slidably circumscribe a path around the examination area 16. Such a linear motor can introduce a degree of translational inaccuracy. The appearance of isolated instances of rotational and translational error compared to an instructed position of the C-arm is already problematic, but the resultant error is amplified when it is taken into account that the error is multiplied across, for example, azimuthal connection 12a, rotatable bearing 12b, and a linear motor connecting the C-bracket to the rotational bearing 12B.

In other words, when the C-arm 12 is instructed by control apparatus 18 to perform a generic orbit around the examination area 16, owing to the geometric deviations, the orbit that the C-arm 12 performs in reality will be different to the orbit that the control apparatus 18 instructs the C-arm 12 to perform. With no correction to account for the geometric deviations caused by the mechanical inaccuracies of the C-arm system, a 3D reconstruction of an acquired 2D projection frame sequence will suffer from high levels of reconstruction error.

The skilled person will appreciate that the above-outlined problem will appear in any coordinate system (Cartesian, polar, parametric) with respect to any datum (examination area 16, for example), and thus in this application will be appreciated that a discussion of errors and geometric deviations from a preferred geometry are relevant in the case of any coordinate system and datum.

A solution to the above-outlined problem is to provide, in the examination area 16, an examination phantom having a known 3D structure. A C-arm system would then be manipulated around the examination area 16 in a series of pre-defined orbital paths. Errors in reconstructions of 2D projection frame sequences of the examination phantom so acquired caused by deviations of the C-arm system from the expected geometry may be used to update expected calibration data of the C-arm system, for example. However, this is not the only source of expected calibration data, which could also arise from a servicing of the C-arm system, for example. However, it is undesirable to use an examination phantom to update the expected calibration data too frequently, because this means that, during calibration, the C-arm system cannot be used for medical interventions.

According to the second aspect, there is provided an error tracking method for calibrating a mechanical image acquisition system, comprising:

a) acquiring at least first and second 2D projection frame sequences of an examination area of the mechanical image acquisition system at different times using the same mechanical image acquisition system in first and second acquisitions;
b) acquiring expected calibration data defining an expected calibrated geometry of the mechanical image acquisition system;
c) applying rigid motion compensation separately to at least the first and second 2D projection sequences and comparing the compensated first and second 2D projection sequences separately to the expected calibrated geometry, to thus generate a first sequence and a second sequence of frame deviation measures representing a geometric deviation of the mechanical image acquisition system from the expected calibrated geometry occurring during the first and second acquisitions;
d) determining a resemblance between the first sequence of frame deviation measures and the second sequence of frame deviation measures; and
e) if a resemblance between at least one portion of the first and second sequences of the frame deviation measures is determined, performing one or more calibration actions.

Figure 2:
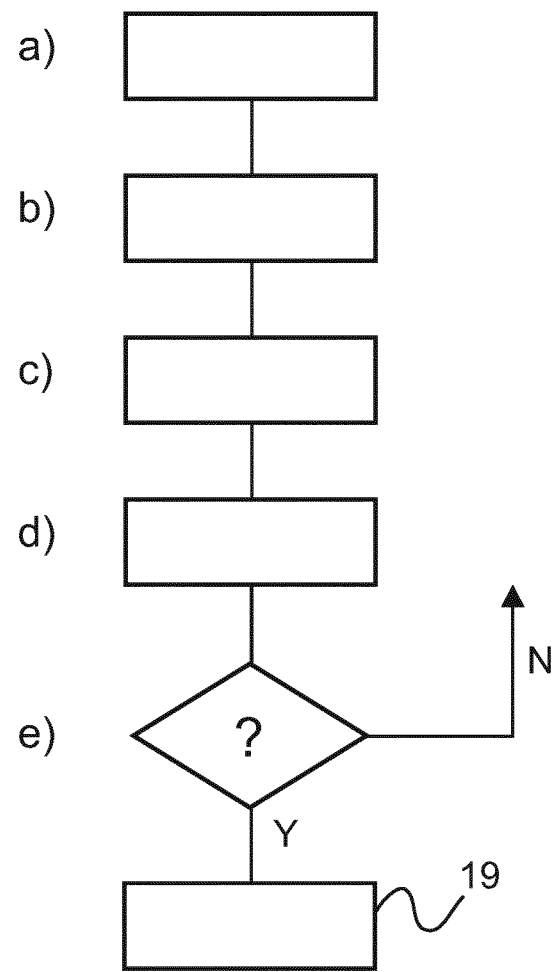
FIG. 2 schematically illustrates a method according to the second aspect.

FIG. 2 schematically illustrates a method according to the second aspect.

In step a), a mechanical image acquisition system is used to obtain at least first and second 2D projection frame sequences although may obtain any plurality of sequences. The sequences are obtained at different times. The sequences may be of the same object (patient), or of different objects (patients). In other words, a first geometrical deviation of the mechanical image acquisition system from its expected calibrated state is obtained in the first 2D projection frame sequence. A second geometrical deviation of the mechanical image acquisition system from its expected calibrated state is obtained in the second 2D projection frame sequence.

Each frame of the 2D projection frame sequence is optionally a two-dimensional intensity map through a section of the examination region 16 obtained by the X-Ray detector 12d. However, other imaging modalities may obtain a one-dimensional slice through the examination area 16, for example. Optionally, the imaging technique applied by the mechanical imaging acquisition system is "cone beam computed tomography" (CBCT).

In step b), expected calibration data is received by a control circuit of the mechanical image acquisition system. The expected calibration data may be provided, for example, from a software module executing on a processor of the mechanical image acquisition system that has previously measured a calibration error using a calibration phantom. Optionally, the expected calibration data may be downloaded from a service laptop personal computer, or provided over a wide area network such as Internet, or received from a vendor server of the mechanical image acquisition system.

The expected calibration data accounts for previously-identified errors in calibration of the mechanical imaging acquisition system. Therefore, for a given imaging acquisition protocol, the previously identified errors may be corrected mechanically or their presence is taken into account during the subsequent data processing. The format of the expected calibration data may take many forms. Optionally, a look-up table is provided having a dimension for each degree of freedom of the mechanical image acquisition system. Therefore, when an acquisition protocol commands the mechanical image acquisition system into a position defined by a series of position values in each degree of freedom, a correction to the acquisition protocol command can be read directly out of the lookup table. Optionally, the expected calibration data may be provided, or supplemented by, by a parameterisible mathematical model, or a database of previously experienced calibration behavior. In this way, the expected calibration data can define expected calibration projection geometry of the mechanical image acquisition system that has previously been measured.

The skilled person will appreciate that up to this point in the method, the mechanical image acquisition system has been furnished with the ability to correct for previously identified calibration errors, but not to identify new calibration errors.

In step c), at least two rigid motion compensations are performed to the first and second 2-D projection sequences. In other words, the orientation of an object in the examination area 16 obtained during the first acquisition and during the second acquisition are separately calculated.

Optionally, the rigid motion compensation is performed for first and second 2D projection frame sequences that are acquired using the same trajectory. Optionally, the rigid motion compensation is performed for portions of the first and second 2D projection frame sequences that are acquired using the same trajectory. Optionally, the condition that the first and second 2D projection frame sequences have used the same trajectory may be identified using first and second input orbit instructions, respectively. Optionally, the condition that the first and second 2-D projection frame sequences have used the same trajectory may be identified from the rigid motion compensations applied to the first and second 2-D projection sequences.

For a plurality of frames of each 2D projection sequence, a frame deviation measure of the mechanical image acquisition system may be provided (per frame number), representing the geometric deviation of the mechanical image acquisition system in at least one degree of freedom from the expected calibrated projection geometry at a specific frame number. The frame deviation measure is optionally calculated by comparing the result of the rigid motion compensation with the expected calibration projection geometry. The result is, for each 2D projection frame sequence, a sequence of frame deviation measures tracking the rotational and/or translational deviation of the C-arm system per frame number.

Figure 3:
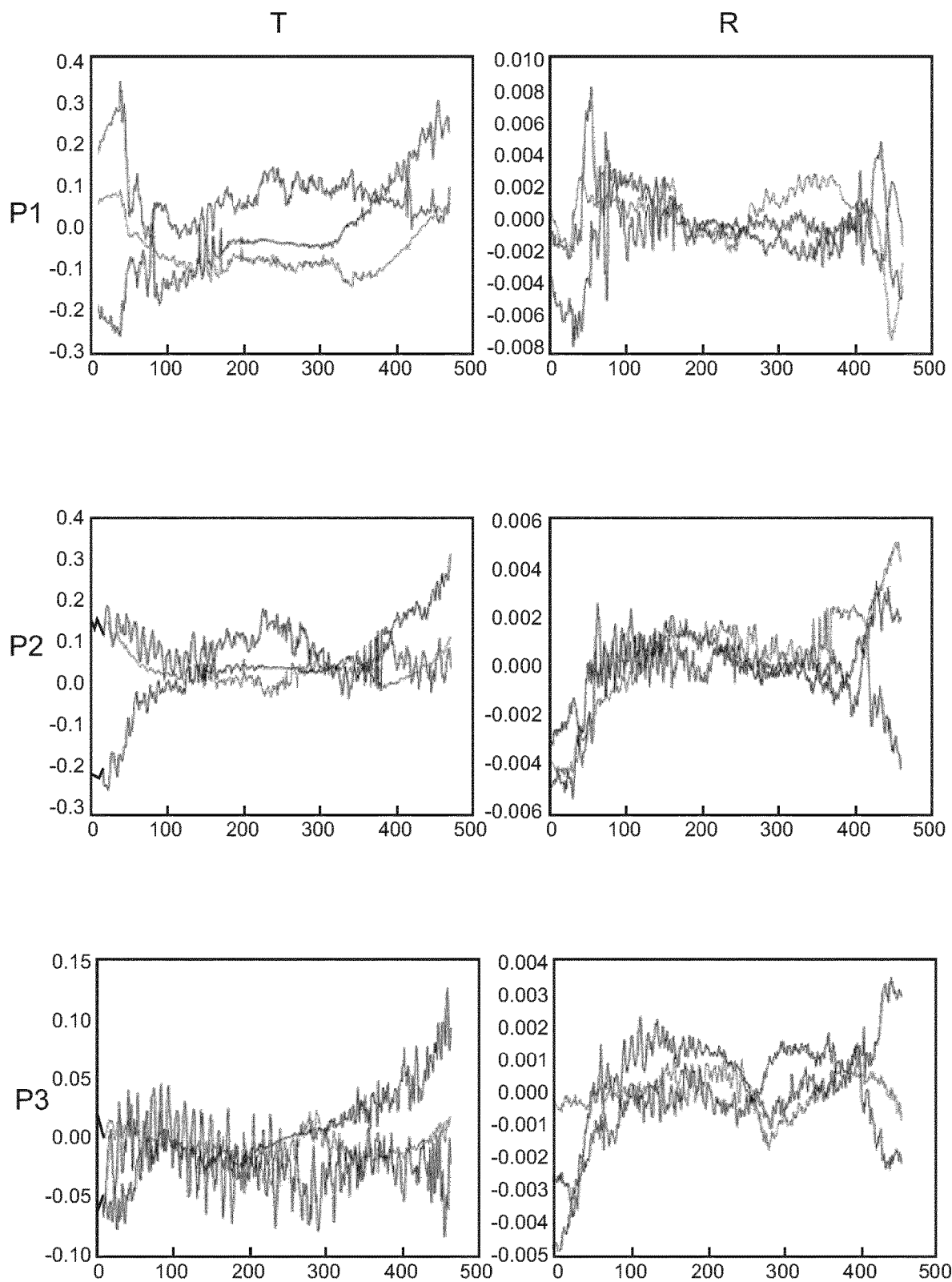
FIG. 3 illustrates geometric transformation parameters plotted over the frame number across a clinical data set of three patients.

FIG. 3 illustrates geometric transformation parameters plotted over the frame number for the motion of a mechanical imaging acquisition system for three clinical datasets of different patients (P1, P2, P3). In this example, a mechanical imaging acquisition system having six degrees of freedom is considered, however the skilled person will realize that a greater or fewer number of degrees of freedom could be tracked. The three lines of each of the plots in the left-hand column (T) track, for each patient, three translational degrees of freedom against frame number. The y-axes of the plots of the left hand column define a translational parameter value (in millimeters) which is a figure of merit of the deviation of the mechanical image acquisition system used in the acquisitions between an ideal case and the measured case. The Y axes of the plots of the right hand column define a rotational parameter value (in radians) which is a figure of merit of the deviation of the mechanical image acquisition system used in the acquisitions between an ideal case and the measured case. The three lines of each of the plots in the right-hand column (R) track, for each patient, three rotational degrees of freedom against frame number.

It can be seen that the parameters are different for all three patients over the duration of the acquisitions.

In step d), the resemblance between the portions of the first and second frame deviation measures is determined, for example, by comparing a plurality of frame deviation measures of the first sequence to a plurality of frame deviation measures of the second sequence. In practice, this comparison is optionally performed, for example, using a cross-correlation between the first and second frame deviation measures, optionally using a sliding window. However, a skilled person will realize that there are many ways to compare the first and second sequences of frame deviation measures to identify the resemblance, and other options could include a pattern-matching approach, the use of a Kalman filter, averaging, local and global similarity measures, feature detection, machine learning, artificial intelligence, or neural networks.

For example, in a C-arm suffering from an azimuth joint having an inaccurately calibrated rotary encoder, the first and second sequences of frame deviation measures in respect of the azimuthal deviation from an ideal case will both contain the same inaccuracy arising from the inaccurately calibrated rotary encoder. Thus, a correlation between the first and second sequences of frame deviation measures would, in this case, be detectable because both of the first and second sequences of frame deviation measures would have the same angular offset when the azimuth joint was rotated.

A skilled person will allow that the example of the foregoing paragraph is applicable to other aspects of the mechanical arrangement of a mechanical image acquisition system, such as a cantilever-type deformation of an imaging arm when an imaging arm is caused, by its orbit, to extend from its support, for example.

In step e), a resemblance of the first and second sequences of the frame deviation measures may be identified, for example, when a cross-correlation of the first and second frame deviation measures exceeds a given threshold. For other comparison techniques listed in the description of step d), similar thresholds can be provided.

Figure 4:
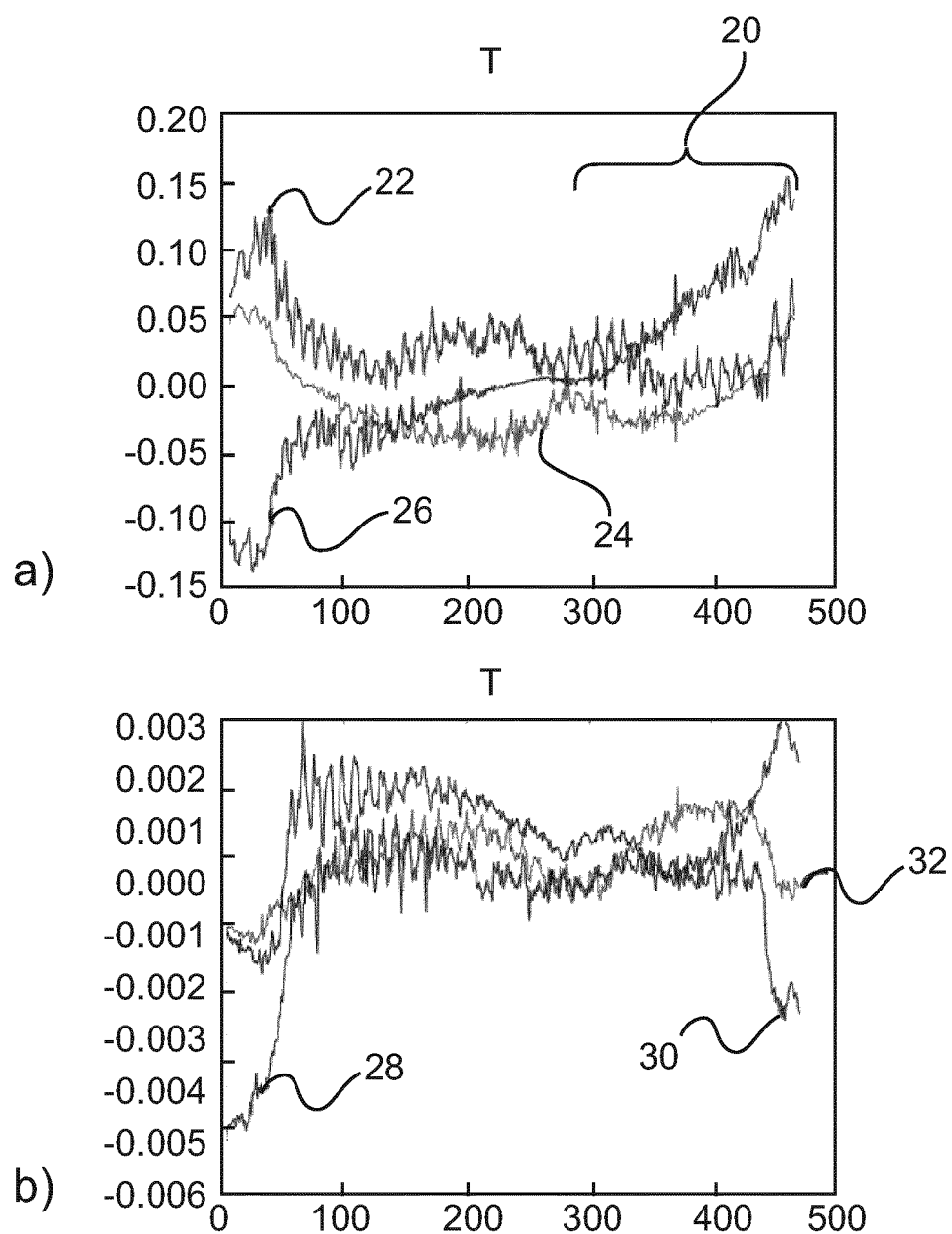
FIG. 4 illustrates average geometric transformation parameters from 10 patients plotted over the frame number for motion corrected trajectories.

FIG. 4 shows averaged geometric transformation parameters from ten patients plotted over the frame number for motion corrected trajectories. FIG. 4a) measures three translational degrees of freedom 22, 24, 26 in millimeters (on the y-axis) against frame number. FIG. 4b) tracks three rotational degrees of freedom 28, 30, and 32 in radians (on the y-axis) against frame number. It is seen that at least at the sector of the graph of FIG. 4a) marked 20, the averaged translational degree of freedom 26 indicates the need for a recalibration of the C-arm geometry, because across a similar range of frame numbers, the same deviation is repeated such that the average across all 10 patients is increased in the same translational degree of freedom. It is noted that translational degree of freedom 24 also shows the same tendency across a similar range of frame numbers.

In step e), one or more calibration actions are performed if, in step d), a resemblance between the first and second sequences of the frame deviation measures is identified. As noted in the definitions section above, the term "calibration action" can mean notifying, by the transmission of a data message over a data network, an external user or maintenance service that the mechanical image acquisition system requires calibration. Optionally, the term calibration action can mean that the mechanical image acquisition system itself automatically performs a calibration routine.

Optionally, the step d) of determining a resemblance between the first sequence of frame deviation measures and the second sequence of frame deviation measures further comprises:

d1) comparing a selected number of the first sequence of frame deviation measures to a selected number of the second sequence of frame deviation measures;

d2) identifying at least a first matching portion of the first and second sequences of the frame deviation measures.

For example, a matching portion between the first and second sequences of the frame deviation measures may be a portion where both sequences of the frame deviation measures follow the same gradient for a given number of frame indices, although the skilled person will appreciate that a wide range of patterns and matches may be identified.

Optionally, applying rigid motion compensation separately to at least the first and second 2D projection sequences further comprises:

c1) generating respective first and second initial 3D reconstructions of the first and second 2D projection sequences;

c2) registering the first initial 3D reconstruction to the first 2D projection frame sequence thereby to generate a first frame offset vector; and c3) registering the second 3D initial 3D reconstruction to the second 2D projection frame sequence thereby to generate a second frame offset vector.

Optionally, applying rigid motion compensation separately to at least the first and second 2D projection sequences further comprises:

c4) generating the first and second sequences of frame deviation measures iteratively by optimizing a first and a second image quality statistic in successive reconstructions of the respective first and second 2D projection sequences.

Optionally, an image quality statistic can be the presence of blurring, and/or "ring artefacts" caused by misalignment of the mechanical imaging acquisition system through poor calibration, although a skilled person can also identify other image quality statistics.

Optionally, the method of the second aspect further comprises:

a1) receiving deviation threshold data of the acquisition system;

e1) identifying a first measured deviation of the mechanical image acquisition system from the expected calibration geometry based on a difference between the portion of the first and second sequences of frame deviation measures and the threshold data for which a resemblance has been determined; and e2) if the first measured deviation exceeds a threshold in the deviation threshold data, performing the calibration action by displaying to a user a maintenance prompt, and/or transmitting a maintenance request over a data communication network to an external maintenance server.

Accordingly, if the detected common patterns surpass a predefined threshold, a maintenance request is displayed, or maintenance is automatically scheduled. The metric used for the threshold criterion may be a Cartesian 3-D distance of the expected and found X-Ray source (or X-Ray detector, or a combination of both) positions calculated as averaged over the full trajectory of the mechanical image acquisition system, or for each frame individually. Many other suitable metrics may also be used.

Optionally, the method of the second aspect further comprises:

a2) acquiring a third 2D projection frame sequence, at a subsequent time to the first and second 2D projection frame sequences;

d3) determining a corresponding third sequence of frame deviation measures of the third 2D projection frame sequence from the expected calibrated geometry, e1) identifying a resemblance between portions of the second and third sequences of the frame deviation measures;

e2) identifying a second measured deviation of the mechanical image acquisition system from the expected calibration geometry between the second and third sequences of the frame deviation measures based upon the resemblance between the portions of the second and third sequences of the frame deviation measures;

e3) predicting, using a rate of change of the difference between the first and second measured deviations, a scheduling time of a future maintenance period; and e3) transmitting, as the calibration action, the scheduling time of the future maintenance period over a data communication network to an external maintenance server, and/or displaying the scheduling time to a user.

Accordingly, by performing the test according to the second aspect for multiple time intervals, changes in the common patterns over time may be used to predict when the threshold criterion will be passed. This can be used to schedule predictive maintenance.

Optionally, the method of the second aspect further comprises:

d4) estimating a first corrected trajectory of the mechanical image acquisition system during the acquisition of the first 2D projection sequence based on the first sequence of frame deviation measures, and estimating a second corrected trajectory of the mechanical image acquisition system during the acquisition of the second mechanical image CT projection sequence based on the second sequence of frame deviation measures.

Optionally, the method of the second aspect further comprises:

d5) identifying selected portions of the first and second corrected trajectories having a significant similarity to each other; and d6) calculating calibration difference data between the selected portions; and wherein performing the calibration action comprises:

e5) acquiring a third 2D projection frame sequence and applying the calibration difference data to generated a corrected third 2D projection frame sequence.

The term "significant similarity" is reliant on the identification method used to compare the selected portions of the first and second corrected trajectories, but may be a threshold of the cross-correlation, for example.

Optionally, the method of the second aspect further comprises:

a3) acquiring a trajectory characteristic database comprising example trajectory data of historical geometry deviations of the mechanical image acquisition system; and wherein the calibration action comprises:

e6) comparing at least one of the selected portions of the first and second corrected trajectories to the example trajectory data in the trajectory characteristic database; and e7) confirming that the at least one of the selected portions of the first and second corrected trajectories resembles a historical geometry deviation of the mechanical image acquisition system.

Accordingly, the found common patterns are compared to a database, or to a trained classifier, to identify which deviations are typical geometry variations that occur over time. Other identified patterns may be false identifications not requiring recalibration.

Optionally, the method of the second aspect further comprises:

a4) receiving and/or automatically identifying an acquisition protocol of the mechanical image acquisition sequence used during the acquisition of the first and/or second 2D projection frame acquisition sequences; and wherein the calibration action comprises:

e8) assigning a confidence level to the first sequence of frame deviation measures based upon the acquisition protocol.

For example, additional patient data may be stored with acquired first and second 2-D projection frame sequences. For example, information about whether the patient was sedated or not during the acquisition. Such information may be used to identify cases where the patient did not move during the acquisition, and thus give this data a higher importance in the comparison and identification steps.

Optionally, specific types of acquisitions may be better suited than others to apply the method according to the second aspect. For example, head C-arm scans have the advantage that strong bone features allowing more accurate rigid motion compensation. The method may therefore be focused only on these types of acquisitions, or these types of acquisitions may be given a higher importance if the findings are inconclusive, or if insufficient data is available. Some individual acquisitions may also be excluded from the analysis if strong patient motion occurs, or if there are other unique differences such as implants which impact reconstruction quality, or any of the other involved algorithms.

Optionally, the first sequence and a second sequence of frame deviation measures comprise a first and second sequence of magnitudes representing the magnitude of respective first and second offset vectors from an ideally calibrated case.

Optionally, the mechanical image acquisition system is a C-arm.

In other words, the second aspect discusses applying a 2D/3D registration method, or another rigid motion compensation method after each CT (for example) acquisition, optionally in the background. The motion corrected trajectories from multiple patients are compared over time. Deviations from the expected mechanical image acquisition system trajectory that are consistent for multiple patients are identified as inaccuracies in the mechanical acquisition system. In this way, the comparison of multiple data-sets allows a focus on deviations that are consistently caused by the mechanical image acquisition system. Patient motion, or other deviations (that cause a unique variation that is independent from the mechanical image acquisition system) are averaged out.

A first optional embodiment displays a maintenance request on an external or internal display of the mechanical image acquisition system, or automatically schedules maintenance if the discovered deviations exceed a predefined threshold. In another embodiment, the geometry calibration of the C-arm system is automatically corrected based on the found deviations.

A summary of the steps provided is:
1) To perform a rigid motion compensation for multiple image acquisitions that are recorded with the same trajectory. In other words, an initial 3D reconstruction is registered to all 2D projections of the rotational acquisition. Alternatively, or in combination an artefact measure, or a sharpness measure in the reconstructed 3D image may be optimized.
2) A corresponding motion corrected trajectory is calculated for each scan.
3) A set of motion corrected trajectories from a recent time interval is selected.
4) the selected motion corrected trajectories are compared with each other, and common patterns are extracted using, for example, averaging, local and global similarity measures, feature detection, machine learning, or neural networks.
5) one or more calibration actions, such as triggering a maintenance request, or automatically calibrating the geometry of mechanical image acquisition system, is generated.

Optionally, the apparatus comprises an output unit 56 for displaying the motion-compensated 3D reconstruction to a user. For example, the output unit 56 may be a computer display. Of course, the output unit could be a data communication means configured to transmit the motion-compensated 3D reconstruction to another computer or display unit. Optionally, the motion-compensated 3D reconstruction can be securely transmitted to a hand-held display or provided to a secure data storage means such as a PACS server.

Figure 5:
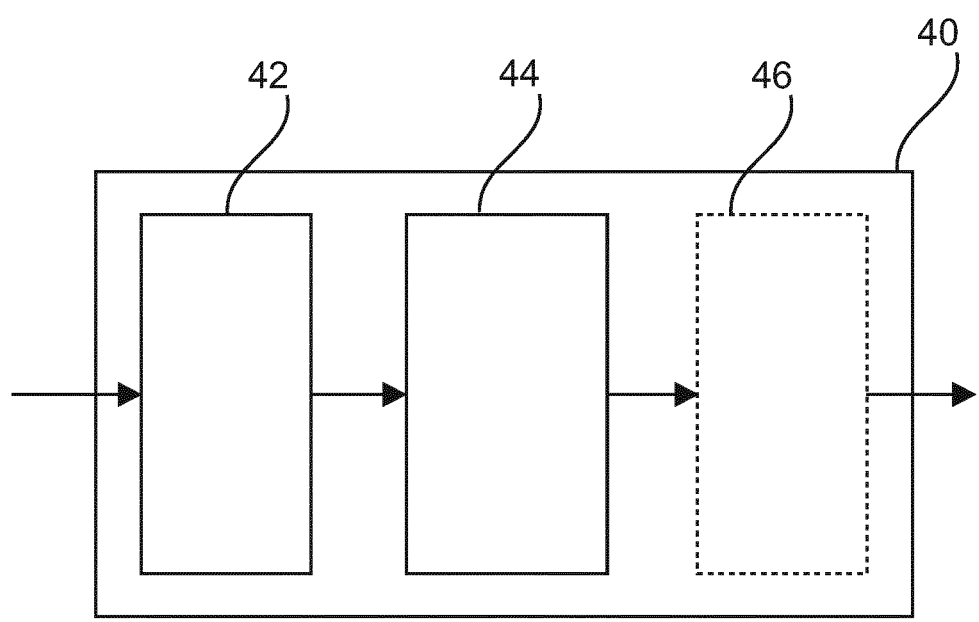
FIG. 5 schematically illustrates as apparatus for performing error tracking and calibration of a mechanical image acquisition system.

FIG. 5 illustrates an apparatus 40 in accordance with the first aspect and its optional embodiments.

According to a first aspect, there is provided an apparatus 40 for performing error tracking and calibration of a mechanical image acquisition system. The apparatus comprises:

an input unit 42; and a processing unit 44.

The input unit 42 is configured to acquire at least first and second 2D projection frame sequences of an examination area of the mechanical image acquisition system at different times using the same mechanical image acquisition system in first and second acquisitions, and to acquire expected calibration data defining an expected calibrated geometry of the mechanical image acquisition system.

The processing unit 44 is configured to apply rigid motion compensation separately to at least the first and second 2D projection sequences and to compare the compensated first and second 2D projection sequences separately to the expected calibrated geometry, to thus generate a first sequence and a second sequence of frame deviation measures representing a geometric deviation of the mechanical image acquisition system from the expected calibrated geometry occurring during the first and second acquisitions, to determine a resemblance between at least a portion of the first sequence of frame deviation measures and at least a portion of the second sequence of frame deviation measures, and, if a resemblance between the respective portions of the first and second sequences of the frame deviation measures is determined, to perform one or more calibration actions.

Optionally, the apparatus is provided as a computer (optionally configured with a graphics processing unit), as function-specific hardware amended, for example, in a field programmable gate array (FPGA) or an application-specific integrated circuit (ASIC). Alternatively, the apparatus can be provided on a centralized server in a PACS system, for example. The input unit 42 is configured to receive input projection image sequences, and first and second 3D rigid object data. However, the skilled person will appreciate the wide range of devices can function to receive such data. For example, the input unit can comprise a connection to an X-Ray tomography or C-arm acquisition system. Optionally, the input unit can comprise a Modem, a LAN or WAN connection, or another data communication means.

The processing unit 44 receives input information from the input unit 42 and processes the input information in accordance with the method discussed in the second aspect discussed above. Optionally, the apparatus 40 may comprise an output unit 46. The output unit can, for example, be a graphics display card to enable the display of 3D reconstruction data, and/or maintenance messages and/or calibration data on a computer monitor. Optionally, the output unit can, for example, comprise a data communication means enabling motion-compensated 3D reconstruction data to be communicated over a secure LAN, WAN, or written to a CD-ROM, DVD-ROM, USB drive, a portable hard-drive, a portable tape-drive or similar.

Optionally, the apparatus may comprise at least the embodiments of the first aspect discussed in the "summary of the invention" section.

According to a third aspect there is provided an X-Ray imaging system 12 comprising:
an X-Ray source 12c;
an X-Ray detector 12d; and
an apparatus 18 for performing error tracking and calibration of a mechanical image acquisition system according to the first aspect or its embodiments.

The X-Ray source 12c is configured to sequentially illuminate a region of interest with X-Ray radiation from a first plurality of acquisition angles.

The X-Ray detector 12d is configured to receive the X-ray radiation having propagated via the region of interest from a second plurality of acquisition angles to form an input projection image sequence comprising at least first and second 2D X-Ray projection data acquired, respectively, at first and second acquisition times of a region of interest of a patient.

The apparatus 18 for performing error tracking and calibration of a mechanical image acquisition system is configured to receive the first and second 2D X-Ray projection data from the X-Ray detector, and the apparatus is configured to receive expected calibration data defining an expected calibrated geometry of the X-Ray imaging system from the X-Ray imaging system.

According to a fourth aspect there is provided a computer program element for controlling a processing unit and/or system according to the first and/or third aspects, which, when the computer program element is executed by the processor and/or system, is adapted to perform the method of the second aspect.

According to a fifth aspect there is provided a computer readable medium having stored the computer program element of the fourth aspect.

A computer program element might therefore be stored on a computer unit, which might also be an embodiment of the present invention. This computing unit may be adapted to perform or induce performance of the steps of the method described above.

Moreover, it may be adapted to operate the components of the above-described apparatus.

The computing unit can be adapted to operate automatically and/or execute orders of a user. A computer program may be loaded into the working memory of a data processor. The data processor may thus be equipped to carry out the method of the invention.

This exemplary embodiment of the invention covers both the computer program that has the invention installed from the beginning, and a computer program that by means of an update turns an existing program into a program that uses the invention. A computer program may be stored and/or distributed on a suitable medium, such as an optical storage medium, or a solid state medium supplied together with, or as part of other hardware, but may also be distributed in other forms, such as via the Internet or other wired or wireless telecommunication systems.

However, the computer program may also be presented over a network like the World Wide Web, and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It should to be noted that embodiments of the invention are described with reference to different subject-matters. In particular, some embodiments are described with reference to method-type claims, whereas other embodiments are described with reference to device-type claims. However, a person skilled in the art will gather from the above, and the following description that, unless otherwise notified, in addition to any combination of features belonging to one type of subject-matter, other combination between features relating to different subject-matters is considered to be disclosed with this application.

All features can be combined to provide a synergetic effect that is more than the simple summation of the features.

While the invention has been illustrated and described in detail in the drawings and foregoing description, such illustration and description are to be considered illustrative or exemplary, and not restrictive. The invention is not limited to the disclosed embodiments.

Other variations to the disclosed embodiments can be understood, and effected by those skilled in the art in practicing the claimed invention, from a study of the drawings, the disclosure, and the dependent claims.

In the claims, the word "comprising" does not exclude other elements or steps, and the indefinite article "a" or "an" does not exclude a plurality. A single processor, or other unit, may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. An apparatus for performing error tracking and calibration of a mechanical image acquisition system, the apparatus comprising:
an input unit configured to acquire at least first and second 2D projection frame sequences of an examination area of the mechanical image acquisition system at different times using the same mechanical image acquisition system in first and second acquisitions, and to acquire expected calibration data defining an expected calibrated geometry of the mechanical image acquisition system; and
a processing unit configured to:
apply rigid motion compensation separately to at least the first and second 2D projection frame sequences and to compare the compensated first and second 2D projection frame sequences separately to the expected calibrated geometry, to thus generate a first sequence of frame deviation measures and a second sequence of frame deviation measures representing a geometric deviation of the mechanical image acquisition system from the expected calibrated geometry occurring during the first and second acquisitions,
determine a resemblance between the first sequence of frame deviation measures and the second sequence of frame deviation measures, and
if a resemblance between at least a portion of the first sequence of frame deviation measures and the second sequence of frame deviation measures is determined, perform one or more calibration actions.

2. The apparatus according to claim 1,
wherein the processing unit is further configured to apply rigid motion compensation separately to at least the first and second 2D projection frame sequences by:
generating respective first and second initial 3D reconstructions of the first and second 2D projection frame sequences;
registering the first initial 3D reconstruction to the first 2D projection frame sequence thereby to generate a first frame offset vector; and
registering the second 3D initial 3D reconstruction to the second 2D projection frame sequence thereby to generate a second frame offset vector.

3. The apparatus according to claim 1,
wherein the processing unit is further configured to apply rigid motion compensation separately to at least the first and second 2D projection frame sequences by:
generating the first sequence of frame deviation measures and the second sequence of frame deviation measures iteratively by optimizing a first and a second image quality statistic in successive reconstructions of the respective first and second 2D projection frame sequences.

4. The apparatus according to claim 1,
wherein the input unit is further configured to:
receive deviation threshold data of the mechanical image acquisition system; and
wherein the processing unit is further configured to:
identify a first measured deviation of the mechanical image acquisition system from the expected calibration geometry based on a difference between the expected calibration geometry and the at least one portion of the first sequence of frame deviation measures and the second sequence of frame deviation measures for which a resemblance has been determined; and
if the first measured deviation exceeds a threshold in the deviation threshold data, to perform the one or more calibration actions by displaying to a user a maintenance prompt, and/or to transmit a maintenance request over a data communication network to an external maintenance server.

5. The apparatus according to claim 4,
wherein the input unit is further configured to:
acquire a third 2D projection frame sequence, at a subsequent time to the first and second 2D projection frame sequences; and
wherein the processing unit is further configured to:
determine a corresponding third sequence of frame deviation measures of the third 2D projection frame sequence from the expected calibrated geometry;
identify a resemblance between the first sequence of frame deviation measures and/or the second sequence of frame deviation measures and the third sequence of frame deviation measures;
identify a second measured deviation of the mechanical image acquisition system from the expected calibration geometry between the first sequence of frame deviation measures and/or the second sequence of frame deviation measures and the third sequences of frame deviation measures based upon the identified resemblance; and
predict, using a rate of change of a difference between the first measured deviation and the second measured deviation, a scheduling time of a future maintenance period; and
wherein the one or more calibration actions comprises transmitting the scheduling time of the future maintenance period over a data communication network to an external maintenance server, and/or displaying the scheduling time to a user.

6. The apparatus according to claim 1,
wherein the processing unit is further configured to:
estimate a first corrected trajectory of the mechanical image acquisition system during acquisition of the first 2D projection frame sequence based on the first sequence of frame deviation measures, and to estimate a second corrected trajectory of the mechanical image acquisition system during acquisition of the second 2D projection frame sequence based on the second sequence of frame deviation measures.

7. The apparatus according to claim 6,
wherein the processing unit is further configured to:
identify selected portions of the first corrected trajectory and the second corrected trajectory having a significant similarity to each other; and
calculate calibration difference data between the selected portions and the expected geometry data;
wherein the processing unit is further configured to perform the one or more calibration actions by:
acquiring a third 2D projection frame sequence and applying the calibration difference data to generate a corrected third 2D projection frame sequence.

8. The apparatus according to claim 7,
wherein the input unit is further configured to:
acquire a trajectory characteristic database comprising example trajectory data of historical geometry deviations of the mechanical image acquisition system; and
wherein the processing unit is further configured to perform as the one or more calibration actions:
comparing at least one of the selected portions of the first corrected trajectory and the second corrected trajectory to the example trajectory data in the trajectory characteristic database; and
confirming that the at least one of the selected portions of the first corrected trajectory and the second corrected trajectory resembles a historical geometry deviation of the mechanical image acquisition system.

9. The apparatus according to claim 1,
wherein the input unit is further configured to:
receive and/or automatically identifying an acquisition protocol, or imaged object of the mechanical image acquisition sequence used during acquisition of the first 2D projection frame acquisition sequence and/or the second 2D projection frame acquisition sequence; and
wherein the processing unit is further configured to perform as the one or more calibration actions:
assigning a confidence level to the first sequence of frame deviation measures based upon the acquisition protocol.

10. The apparatus according to claim 1,
wherein the first sequence of frame deviation measures and the second sequence of frame deviation measures comprise a first and second sequence of magnitudes representing a magnitude of respective first and second offset vectors from an ideally calibrated case.

11. The apparatus according to claim 1,
wherein the mechanical image acquisition system is a C-arm.

12. An error tracking method for calibrating a mechanical image acquisition system, the method comprising:
- acquiring at least first and second 2D projection frame sequences of an examination area of the mechanical image acquisition system at different times using the same mechanical image acquisition system in first and second acquisitions;
- acquiring expected calibration data defining an expected calibrated geometry of the mechanical image acquisition system;
- applying rigid motion compensation separately to at least the first and second 2D projection frame sequences and comparing the compensated first and second 2D projection frame sequences separately to the expected calibrated geometry, to thus generate a first sequence of frame deviation measures and a second sequence of frame deviation measures representing a geometric deviation of the mechanical image acquisition system from the expected calibrated geometry occurring during the first and second acquisitions;
- determining a resemblance between the first sequence of frame deviation measures and the second sequence of frame deviation measures; and
- if a resemblance between at least one portion of the first sequence of frame deviation measures and the second sequence of frame deviation measures is determined, performing one or more calibration actions.

13. An X-Ray imaging system comprising:
- an apparatus for performing error tracking and calibration of the mechanical image acquisition system according to claim 1;
- an X-Ray source configured to sequentially illuminate a region of interest with X-Ray radiation from a first plurality of acquisition angles;
- an X-Ray detector configured to receive the X-ray radiation having propagated via the region of interest from a second plurality of acquisition angles to form an input projection image sequence comprising at least first and second 2D X-Ray projection data acquired, respectively, at first and second acquisition times of a region of interest of a patient; and
- the apparatus for performing error tracking and calibration of the mechanical image acquisition system configured to receive the first and second 2D X-Ray projection data from the X-Ray detector and receive expected calibration data defining an expected calibrated geometry of the X-Ray imaging system from the X-Ray imaging system.

14. A non-transitory computer-readable storage medium having stored a computer program comprising instructions for controlling an apparatus for performing error tracking and calibration of a mechanical image acquisition system, the instructions, when executed by a processor, cause the processor to:
- acquire at least first and second 2D projection frame sequences of an examination area of the mechanical image acquisition system at different times using the same mechanical image acquisition system in first and second acquisitions, and to acquire expected calibration data defining an expected calibrated geometry of the mechanical image acquisition system;
- apply rigid motion compensation separately to at least the first and second 2D projection frame sequences and to compare the compensated first and second 2D projection frame sequences separately to the expected calibrated geometry, to thus generate a first sequence of frame deviation measures and a second sequence of frame deviation measures representing a geometric deviation of the mechanical image acquisition system from the expected calibrated geometry occurring during the first and second acquisitions;
- determine a resemblance between the first sequence of frame deviation measures and the second sequence of frame deviation measures; and
- if a resemblance between at least a portion of the first sequence of frame deviation measures and the second sequence of frame deviation measures is determined, perform one or more calibration actions.

* * * * *